United States Patent [19]

Cramp et al.

[11] Patent Number: 5,371,064
[45] Date of Patent: Dec. 6, 1994

[54] HERBICIDAL 4-BENZOYLISOXAZOLE DERIVATIVES

[75] Inventors: Susan M. Cramp; Claude Lambert; John Morris, all of Ongar Essex, England

[73] Assignee: Rhone-Poulenc Argriculture Ltd, Essex, England

[21] Appl. No.: 94,967

[22] Filed: Jul. 22, 1993

[30] Foreign Application Priority Data

Jul. 22, 1992 [GB] United Kingdom ............... 9215551

[51] Int. Cl.$^5$ ............... A01N 43/80; C07D 261/06
[52] U.S. Cl. ............... 504/271; 548/248
[58] Field of Search ............... 548/248; 504/271, 349, 504/350, 351, 352, 348

[56] References Cited

U.S. PATENT DOCUMENTS 4,957,540  9/1990  Knudsen et al. ............... 504/348

FOREIGN PATENT DOCUMENTS 0418175  3/1991  European Pat. Off.
0487357  5/1992  European Pat. Off.

Primary Examiner—Richard L. Raymond
Assistant Examiner—Mary C. Cebulak
Attorney, Agent, or Firm—Burns, Doane, Swecker & Mathis

[57] ABSTRACT

4-Benzoylisoxazole derivatives of formula (I):

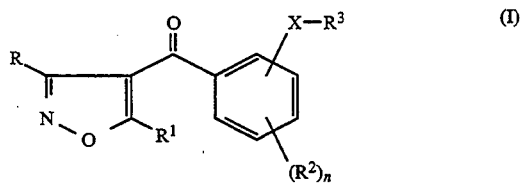

wherein:
  R represents hydrogen or $-CO_2R^4$;
  $R^1$ represents alkyl, haloalkyl or optionally substituted cycloalkyl;
  $R^2$ represents halogen, alkyl, haloalkyl or alkyl substituted by $-OR^5$, or a group selected from nitro, cyano, $-CO_2R^4$, $-S(O)_pR^6$, $-O(CH_2)_rOR^5$ and $-OR^5$;
  $R^3$ represents optionally substituted phenyl;
  X represents oxygen or $-S(O)-_q$;
  n represents zero or an integer from one to four;
  $R^4$ and $R^5$ independently represent alkyl or haloalkyl;
  $R^6$ represents alkyl, haloalkyl or optionally substituted phenyl;
  $R^7$ represents halogen, alkyl or haloalkyl or a group selected from nitro, cyano, $-OR^5$ and $-S(O)_pR^6$;
  p represents 0, 1 or 2; q represents 0, 1 or 2;
  r represents 1, 2 or 3;
  the herbicidal properties of these derivatives and their application to crop protection are described.

33 Claims, No Drawings

HERBICIDAL 4-BENZOYLISOXAZOLE DERIVATIVES

This invention relates to novel 4-benzoylisoxazole derivatives, compositions containing them, processes for their preparation. intermediates in their preparation and their use as herbicides.

The present invention provides 4-benzoylisoxazole derivatives of formula (I):

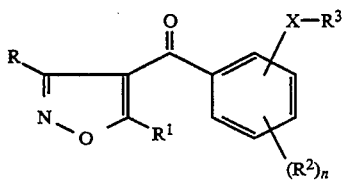

wherein:

R represents the hydrogen atom or a group $-CO_2R^4$;

$R^1$ represents:
a straight- or branched-chain alkyl group containing up to 6 carbon atoms which is optionally substituted by one or more halogen atoms; or
a cycloalkyl group containing from 3 to 6 carbon atoms optionally substituted by one or more groups $R^5$ or one or more halogen atoms;

$R^2$ represents :a
a halogen atom;
a straight- or branched-chain alkyl group containing up to 6 carbon atoms which is optionally substituted by one or more halogen atoms;
a straight- or branched-chain alkyl group containing up to 6 carbon atoms which is substituted by one or more groups $-OR^5$; or
a group selected from nitro, cyano, $-CO_2R^4$, $-S(O)_pR^6$, $-O(CH_2)_rOR^5$ and $-OR^5$;

$R^3$ represents phenyl optionally substituted by from one to five groups $R^7$ which may be the same or different;

X represents the oxygen atom or $-S(O)_q-$;

n represents zero or an integer from one to four; when n is greater than one the groups $R^2$ may be the same or different;

$R^4$ and $R^5$, which may be the same or different, each represents a straight- or branched-chain alkyl group containing up to 6 carbon atoms which is optionally substituted by one or more halogen atoms;

$R^6$ represents a straight- or branched- chain alkyl group containing up to 6 carbon atoms which is optionally substituted with one or more halogen atoms; or
phenyl optionally substituted by one or more groups $R^7$ which may be the same or different;

$R^7$ represents:
a halogen atom; or
a straight- or branched-chain alkyl group containing up to three carbon atoms which is optionally substituted by one Or more halogen atoms; or
a group selected from nitro, cyano, $-OR^5$ and $-S(O)_pR^6$;

p represents 0, 1 or 2;
q represents 0, 1 or 2;
r represents 1, 2 or 3;
which possess valuable herbicidal properties.

In certain cases the groups R, $R^1$, $R^2$, and $R^3$ may give rise to stereo- and/or optical isomers. All such forms are embraced by the present invention.

A preferred class of compounds of formula (I) are those wherein $R^6$ represents a straight- or branched-chain alkyl group containing up to 6 carbon atoms which is optionally substituted by one or more halogen atoms.

A further preferred class of compounds of formula (I) are those wherein one of the substituents $-XR^3$ or $R^2$ is in the 2-position of the benzoyl ring.

A further preferred class of compounds of formula (I) are those wherein:

$R^1$ represents a straight- or branched- chain alkyl group containing from one to three carbon atoms; or a cyclopropyl group optionally substituted by a group $R^5$;

$R^1$ represents a straight- or branched- chain alkyl group containing from one to three carbon atoms; or a cyclopropyl group optionally substituted by a group $R^5$;

$R^2$ represents:
a halogen atom;
a straight- or branched- chain alkyl group containing up to 6 carbon atoms optionally substituted by one or more halogen atoms;
a straight- or branched- chain alkyl group containing up to 6 carbon atoms, substituted by one or more groups $-OR^5$; or
a group selected from cyano, $-CO_2R^4$, $-S(O)_pR^6$, $-O(CH_2)_rOR^5$ and $-OR^5$;

n represents zero, one or two;

$R^4$ represents a straight- or branched-chain alkyl group containing up to six carbon atoms;

$R^5$ represents a straight- or branched- chain alkyl group containing from one to three carbon atoms which is optionally substituted by one or more halogen atoms; and $R^6$ represents a straight- or branched- chain alkyl group containing from one to three carbon atoms.

A further preferred class of compounds of formula (I) are those wherein:

$R^2$ represents $-S(O)_pR^6$;
one of p or q represents zero.

A further preferred class of compounds of formula (I) are those wherein:

$R^1$ represents methyl, isopropyl, 1-methylcyclopropyl or cyclopropyl;

$R^2$ represents:
a halogen atom; or
a straight- or branched- chain alkyl group containing up to three carbon atoms optionally substituted by one or more halogen atoms; or
a straight- or branched- chain alkyl group containing from one to three carbon atoms optionally substituted by one or more groups $-OR^5$;
or a group selected from $-OR^5$ and $-S(O)_pR^6$;

X represents $-S(O)_q-$;
n represents one or two;

$R^5$ represents a methyl or ethyl group which is optionally substituted by one or more halogen atoms; and $R^6$ represents a methyl or ethyl group.

Further preferred compounds of formula (I) are those wherein the 5- and/or 6- position of the benzoyl ring is unsubstituted, more especially preferred both the 5- and 6- positions are unsubstituted.

A further preferred class of compounds of formula (I) are those wherein:

$R^1$ represents a cyclopropyl group;

$R^2$ represents a halogen atom or a group selected from methyl, trifluoromethyl, methoxy and —S(O)$_p$R$^6$;

n represents one or two;

X represents —S(O)$_q$—;

$R^4$ represents a straight- or branched-chain alkyl group containing up to three carbon atoms;

$R^7$ represents a halogen atom or a group selected from methyl, trifluoromethyl, nitro and —OR$^5$;

$R^5$ represents methyl or ethyl; and $R^6$ represents methyl.

Particularly important compounds of formula (I) include the following:

1. 5-cyclopropyl-4-(2-phenylsulphenyl-4-trifluoromethylbenzoyl)isoxazole;
2. 5-cyclopropyl-4-(2-phenylsulphonyl-4-trifluoromethylbenzoyl)isoxazole;
3. 5-cyclopropyl-4-(2-phenoxy-4-trifluoromethylbenzoyl)isoxazole;
4. 5-cyclopropyl-4-[2-(3-chlorophenylsulphenyl)-4-trifluoromethylbenzoyl]isoxazole;
5. 5-cyclopropyl-4-[2-(2-chlorophenylsulphenyl)-4-trifluoromethylbenzoyl]isoxazole;
6. 5-cyclopropyl-4-[2-(4-chlorophenylsulphenyl)-4-trifluoromethylbenzoyl]isoxazole;
7. 5-cyclopropyl-4-[2-(3-chlorophenylsulphonyl)-4-trifluoromethylbenzoyl]isoxazole;
8. 5-cyclopropyl-4-[2-(4-chlorophenylsulphonyl)-4-trifluoromethylbenzoyl]isoxazole;
9. 5-cyclopropyl-4-[2-(4-chlorophenylsulphenyl)-4-trifluoromethylbenzoyl]isoxazole;
10. 5-cyclopropyl-4-(4-chloro-2-phenylsulphenylbenzoyl)isoxazole;
11. 5-cyclopropyl-4-(4-chloro-2-phenylsulphonylbenzoyl)isoxazole;
12. 5-cyclopropyl-4-[4-chloro-2-(3-chlorophenylsulphenyl)benzoyl]isoxazole;
13. 5-cyclopropyl-4-[4-chloro-2-(3-chlorophenylsulphinyl)benzoyl]isoxazole;
14. 5-cyclopropyl-4-[4-chloro-2-(3-chlorophenylsulphonyl)benzoyl]isoxazole;
15. 5-cyclopropyl-4-[4-chloro-2-(3-methoxyphenylsulphenyl)benzoyl]isoxazole;
16. 5-cyclopropyl-4-[4-chloro-2-(3-methoxyphenylsulphinyl)benzoyl]isoxazole;
17. 5-cyclopropyl-4-[4-chloro-2-(3-methoxyphenylsulphonyl)benzoyl]isoxazole;
18. 5-cyclopropyl-4-[2,4-bis(phenylsulphenyl)benzoyl]isoxazole;
19. 5-cyclopropyl-4-(3,4-dichloro-2-phenylsulphenylbenzoyl)isoxazole;
20. 5-cyclopropyl-4-(3,4-dichloro-2-phenylsulphonylbenzoyl)isoxazole;
21. 5-cyclopropyl-4-(4-chloro-2-methylsulphonyl-3-phenoxybenzoyl)isoxazole;
22. 5-cyclopropyl-4-(4-chloro-2-methylsulphonyl-3phenylsulphenylbenzoyl)isoxazole; and
23. 5-cyclopropyl-4-(2-methylsulphonyl-3-phenylsulphenylbenzoyl)isoxazole.

The numbers 1 to 23 are assigned to these compounds for reference and identification hereafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen may be prepared by the reaction of a compound of formula (II):

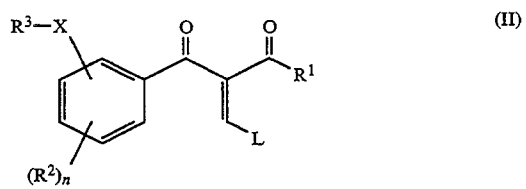

wherein $R^1$, $R^2$, $R^3$, X and n are as hereinbefore defined, and L is a leaving group, with hydroxylamine or a salt of hydroxylamine. Hydroxylamine hydrochloride is generally preferred. Generally L is O-alkyl, for example ethoxy, or N,N-dialkylamino, for example N,N-dimethylamino. The reaction is generally carried out in an organic solvent such as ethanol or acetonitrile or a mixture of a water-miscible organic solvent and water, preferably in a ratio of organic solvent: water of from 1:99 to 99:1. optionally in the presence of a base or acid acceptor such as triethylamine or sodium acetate at a temperature from 0° to 100° C.

According to a further feature of the present invention compounds of formula (I) in which R represents hydrogen may be prepared by the reaction of a compound of formula (III):

wherein $R^1$ is as hereinbefore defined and Y represents a carboxy group or a reactive derivative thereof (such as a carboxylic acid chloride or carboxylic ester), or a cyano group, with an appropriate organometallic reagent such as a Grignard reagent or an organolitlaium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —CO$_2$R$^4$ in which R$^4$ is as hereinbefore defined, may be prepared by the reaction of a compound of formula (IV)

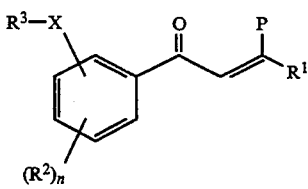
(IV)

wherein
$R^1$, $R^2$, $R^3$, X and n are as hereinbefore defined and P is a leaving group such as N,N-dialkylamino, with a compound of formula $R^4O_2CC(Z)=NOH$ wherein $R^4$ is as hereinbefore defined and Z is a halogen atom. Generally Z is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula (I) in which R represents a group —$CO_2R^4$ in which $R^4$ is as hereinbefore defined, may be prepared by the reaction of compounds of formula (V):

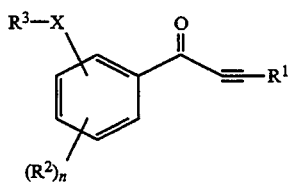
(V)

wherein
$R^1$, $R^2$, $R^3$, X and n are as hereinbefore defined with compounds of formula $R^4O_2CC(Z)=NOH$ wherein $R^4$ and Z are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents —$CO_2R^4$ and $R^4$ is as hereinbefore defined may be prepared by the reaction of a salt of compounds of formula (VI):

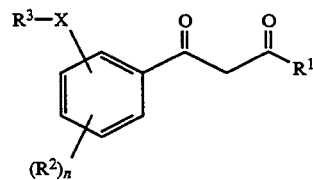
(VI)

wherein
$R^1$, $R^2$, $R^3$, X and n are as hereinbefore defined, with a compound of formula $R^4O_2CC(Z)=NOH$ wherein $R^4$ and Z are as hereinbefore defined. Preferred salts include sodium or magnesium salts. The reaction may be performed in an inert solvent such as dichloromethane or acetonitrile at a temperature between room temperature and the reflux temperature of the mixture.

Intermediates in the preparation of compounds of formula (I) may be prepared by the application or adaptation of known methods.

Compounds of formula (II) in which L represents O-alkyl or N,N-dialkylamino may be prepared by the reaction of compounds of formula (VI) with either a trialkyl orthoformate such as triethyl orthoformate or a dimethylformamide dialkyl acetal such as dimethylformamide dimethyl acetal. The reaction with triethyl orthoformate is generally carried out in the presence of acetic anhydride at the reflux temperature of the mixture and the reaction with dimethylformamide dialkyl acetal is carried out optionally in the presence of an inert solvent at a temperature from room temperature to the reflux temperature of the mixture.

Intermediates of formula (IV) may be prepared by the reaction of a compound of formula (VII) wherein $R^1$ and P are as hereinbefore defined with a benzoyl chloride of formula (VIII):

(VII)

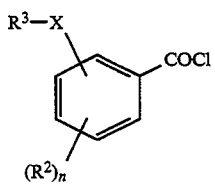
(VIII)

wherein
$R^2$, $R^3$, X and n are as hereinbefore defined. The reaction is generally carried out in the presence of an organic base such as triethylamine in an inert solvent such as toluene or dichloromethane at a temperature between −20° C. and room temperature.

Intermediates of formula (V) may be prepared by the metallation of the appropriate acetylene of formula (IX):

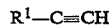
$R^1$—C≡CH    (IX)

wherein
$R^1$ is as hereinbefore defined followed by reaction of the metal salt thus obtained with a benzoyl chloride of formula (VIII). The metallization is generally performed using n-butyl lithium in an inert solvent such as ether or tetrahydrofuran at a temperature from −78° C. to 0° C. The subsequent reaction with the benzoyl chloride is carried out in the same solvent at a temperature between −78° C. and room temperature.

Intermediates of formula (III), (VI), (VII), (VIII) and (IX) are known or may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p is one or two and/or q is one or two may be prepared by the oxidation of the sulphur atom of the corresponding compounds in which p and/or q is zero or one. The oxidation of the sulphur atom is generally carried out using for example 3-chloroperoxybenzoic acid in an inert solvent such as dichloromethane at a temperature from −40° C. to room temperature, or using hydrogen peroxide in acetic acid in the presence of acetic anhydride or concentrated sulphuric acid.

The following examples illustrate the preparation of compounds of formula (I) and the following reference examples illustrate the preparation of intermediates of the invention. In the present specification b.p. means boiling point; m.p. means melting point. Where the letters NMR appear the characteristics of the proton nuclear magnetic resonance spectrum follow.

EXAMPLE 1

A mixture of 3-cyclopropyl-2-ethoxymethylene-1-(2-phenylsulphenyl-4-trifluoromethylphenyl)propan-1,3-dione (7 g), hydroxylamine hydrochloride (1.24 g) and sodium acetate (1.5 g) in ethanol was stirred at 25° C. for 2 hours. The mixture was then poured into water and extracted with ethyl acetate. The solution was dried over anhydrous sodium sulphate and filtered. The filtrate was evaporated and the residue purified by column chromatography on silica, using a mixture of ethyl acetate and hexane as eluent. The resulting solution was evaporated and the residue crystallized from cyclohexane to give 3.06 g of 5-cyclopropyl-4-(2-phenylsulphenyl-4-trifluoromethylbenzoyl)isoxazole (compound 1), m.p. 115° C.

By proceeding in a similar manner the following compounds of formula (I) were prepared:

| Cpd | R | $R^1$ | $(R^2)_n$ | X | $R^3$ | Position of $-X-R^3$ | m.p. NMR |
|---|---|---|---|---|---|---|---|
| 3 | H | Cp | 4-$CF_3$ | O | $C_6H_5$ | 2 | 100° C. |
| 4 | H | Cp | 4-$CF_3$ | S | 3-Cl—$C_6H_4$ | 2 | 106.1° C. |
| 5 | H | Cp | 4-$CF_3$ | S | 2-Cl—$C_6H_4$ | 2 | 59.7° C. |
| 6 | H | Cp | 4-$CF_3$ | S | 4-Cl—$C_6H_4$ | 2 | Oil (a) |
| 10 | H | Cp | 4-Cl | S | $C_6H_5$ | 2 | 73.3° C. |
| 12 | H | Cp | 4-Cl | S | 3-Cl—$C_6H_4$ | 2 | Oil (b) |
| 15 | H | Cp | 4-Cl | S | 3-MeO—$C_6H_4$ | 2 | 64.9° C. |
| 18 | H | Cp | 4-PhS | S | $C_6H_5$ | 2 | 85.5° C. |
| 19 | H | Cp | 3,4-$Cl_2$ | S | $C_6H_5$ | 2 | 92.3° C. |
| 21 | H | Cp | 2-$MeSO_2$-4-Cl | O | $C_6H_5$ | 3 | 105–106° C. |
| 22 | H | Cp | 2-$MeSO_2$-4-Cl | S | $C_6H_5$ | 3 | 159.5° C. |
| 23 | H | Cp | 2-$MeSO_2$ | S | $C_6H_5$ | 3 | 122.0° C. |

Note:
Cp represents cyclopropyl
(a) NMR ($CDCl_3$) 1.2(2H, m), 1.3(2H, m), 2.7(1H, m), 7.3(4H, s), 7.4(1H, m), 7.5(1H, m), 7.6(1H, m), 8.2(1H, s)
(b) NMR ($CDCl_3$) 1.2(2H, m), 1.4(2H, m), 2.7(1H, m), 7.1(1H, m), 7.3(4H, m), 7.4(2H, m), 8.2(1H, s).

EXAMPLE 2

A mixture of 5-cyclopropyl-4-(2-phenylsulphenyl-4-trifluoromethylbenzoyl)isoxazole (1 g) and 3-chloroperoxybenzoic acid (1 g) in dichloromethane was stirred at room temperature for 1 hour. The precipitate was filtered and the flitrate washed with aqueous sodium metabisulphite, aqueous sodium bicarbonate, dried over anhydrous sodium sulphate and filtered. The dichloromethane was evaporated to give 5-cyclopropyl-4-(2-phenylsulphonyl-4-trifluoromethylbenzoyl)isozazole (compound 2, 0.85 g) as a whim solid, m.p. 174° C.

By proceeding in a similar manner the following compounds of formula (I) were prepared:

| Cpd | R | $R^1$ | $(R^2)_n$ | $R^3$ | X | Position of $-X-R^3$ | m.p. |
|---|---|---|---|---|---|---|---|
| 7 | H | Cp | 4-$CF_3$ | 3-Cl—$C_6H_4$ | $SO_2$ | 2 | 135.4° C. |
| 8 | H | Cp | 4-$CF_3$ | 4-Cl—$C_6H_4$ | $SO_2$ | 2 | 173.8° C. |
| 11 | H | Cp | 4-Cl | $C_6H_5$ | $SO_2$ | 2 | 169.6° C. |
| 14 | H | Cp | 4-Cl | 3-Cl—$C_6H_4$ | $SO_2$ | 2 | 132.9° C. |
| 17 | H | Cp | 4-Cl | 3-MeO—$C_6H_4$ | $SO_2$ | 2 | 159.0° C. |
| 20 | H | Cp | 3,4-$Cl_2$ | $C_6H_5$ | $SO_2$ | 2 | 162.4° C. |

EXAMPLE 3

A mixture of 5-cyclopropyl-4-[2-(4-chlorophenylsulphenyl)-4-trifluoromethylbenzoyl]isoxazole (1.14 g) and 3-chloroperoxybenzoic acid (0.84 g) in dichloromethane was stirred at −12° C. for 15 minutes. The precipitate was filtered and the filtrate was washed with aqueous sodium metabisulphite, aqueous sodium bicarbonate and a solution of brine and ammonium chloride, dried over anhydrous sodium sulphate and filtered. The dichloromethane was evaporated and the residue was crystallised from ethanol to give 5-cyclopropyl-4-[2-(4-chlorophenylsulphinyl)-4-trifluoromethylbenzoyl]isoxazole (compound 9, 0.86 g) as white crystals, m.p. 151° C.

By proceeding in a similar mariner the following compounds of formula (I) were prepared:

| Cpd | R | $R^1$ | $R^3$ | $(R^2)_n$ | Position of $-X-R^3$ | X | m.p./°C. |
|---|---|---|---|---|---|---|---|
| 13 | H | Cp | 3-Cl—$C_6H_4$ | 4-Cl | 2 | S(O) | 108.8 |
| 16 | H | Cp | 3-MeO—$C_6H_4$ | 4-Cl | 2 | S(O) | 130.3 |

Note:

Cp represents cyclopropyl

REFERENCE EXAMPLE 1

A mixture of 3-cyclopropyl-1-[2-(4-chlorophenylsulphenyl)-4-trifluoromethylphenyl]propan-1,3-dione (2.9 g) and triethylorthoformate (2.3 g) in acetic anhydride (2.4 g) was heated at reflux for 75 minutes. The reaction mixture was concentrated to give 3-cyclopropyl- 1-[2-(4-chlorophenylsulphenyl)-4-trifluoromethylphenyl]-2-ethoxymethylenepropan-1,3-dione as a red oil which was used without further purification.

By proceeding in a similar manner the following compounds were prepared:

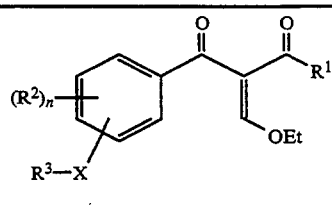

| R¹ | (R²)ₙ | X | R³ | Position of —X—R³ |
|---|---|---|---|---|
| Cp | 4-CF₃ | S | C₆H₅ | 2 |
| Cp | 4-CF₃ | O | C₆H₅ | 2 |
| Cp | 4-CF₃ | S | 3-Cl—C₆H₄ | 2 |
| Cp | 4-CF₃ | S | 2-Cl—C₆H₄ | 2 |
| Cp | 4-Cl | S | C₆H₅ | 2 |
| CP | 4-Cl | S | 3-Cl—C₆H₄ | 2 |
| Cp | 4-Cl | S | 3-MeO—C₆H₄ | 2 |
| Cp | 4-PhS | S | C₆H₅ | 2 |
| Cp | 3,4-Cl₂ | S | C₆H₅ | 2 |
| Cp | 2-MeSO₂-4-Cl | O | C₆H₅ | 3 |
| Cp | 2-MeSO₂-4-Cl | S | C₆H₅ | 3 |
| Cp | 2-MeSO₂ | S | C₆H₅ | 3 |

Note:
Cp represents cyclopropyl

REFERENCE EXAMPLE 3

A solution of methyl 2-phenylsulphenyl-4-trifluoromethylbenzoate (8 g) and cyclopropyl methyl ketone (4.2 g) in tetrahydrofuran was added to a suspension of sodium hydride (1.658 of 80% NaH in oil) in tetrahydrofuran at 60° C. After the addition was complete the temperature was kept at 60° C. for a further 15 minutes. The mixture was then cooled to 25° C. and poured into water. An aqueous solution of hydrochloric acid was added to the mixture to pH 1. The mixture was extracted with ethyl acetate, dried over anhydrous sodium sulphate, filtered and evaporated. The residue was purified by chromatography on silica, using ethyl acetate as eluent to give, after evaporation of the solvent, 3-cyclopropyl-1-(2-phenylsulphenyl-4-trifluoromethylphenyl)propan-1,3-dione as a red oil (8.07 g), NMR (CDCl₃) 0.9(2H,m), 1.25 (2H,m), 1.70(1H, m), 6.05(1H, s), 7.1(1H, s), 7.3-7.5(6H,m), 7.6(1H,s), 15.9(1H,bs).

By proceeding in a similar manner the following diones of formula (VI) were prepped:

| R¹ | (R²)ₙ | X | R³ | Position of -X-R³ | m.p. |
|---|---|---|---|---|---|
| Cp | 4-CF₃ | O | C₆H₅ | 2 | — |
| Cp | 4-CF₃ | S | 3-Cl—C₆H₄ | 2 | — |
| Cp | 4-CF₃ | S | 2-Cl—C₆H₄ | 2 | — |
| Cp | 4-CF₃ | S | 4-Cl—C₆H₄ | 2 | 82° C. |
| Cp | 4-Cl | S | C₆H₅ | 2 | — |
| Cp | 4-Cl | S | 3-Cl—C₆H₄ | 2 | — |
| Cp | 4-Cl | S | 3-MeO—C₆H₄ | 2 | — |
| Cp | 4-PhS | S | C₆H₅ | 2 | — |
| Cp | 3,4-Cl₂ | S | C₆H₅ | 2 | — |

Note:
Cp represents cyclopropyl

REFERENCE EXAMPLE 3

A mixture of t-butyl 2-cyclopropylcarbonyl-3-(2-methylsulphonyl-3-phenylsulphenylphenyl)-3-oxopropionate (8.5 g) and para-toluene sulphonic acid (0.25 g) in toluene was heated at reflux for six hours. Water and ethyl acetate were then added and the organic phase was dried over anhydrous sodium sulphate, filtered and evaporated. The residue was crystallised from ether to give 1-cyclopropyl-3-(2-methylsulphonyl-3-phenylsulphenylphenyl)propan-1,3-dione (6.2 g) as a beige powder, By proceeding in a similar manner the following diones of formula (VI) were prepared:

| R¹ | (R²)ₙ | X | R³ | Position of —X—R³ |
|---|---|---|---|---|
| Cp | 2-MeSO₂-4-Cl | S | C₆H₅ | 3 |
| Cp | 2-MeSO₂-4-Cl | O | C₆H₅ | 3 |

REFERENCE EXAMPLE 4

A mixture of 2-phenylsulphenyl-4-trifluoromethylbenzoic acid (11.5 g), thionyl chloride (1 1.4 g), dimethylformamide (0.2 ml) and dichloroethane was heated at reflux for 90 minutes. The solution was then concentrated under reduced pressure and the residue was dissolved in methanol and heated at reflux for one hour. The resulting solution was poured into aqueous sodium bicarbonate and extracted with ether. The organic phase was dried over anhydrous sodium sulphate, filtered and evaporated. The resulting material was crystallised from hexane to give methyl 2-phenylsulphenyl-4-trifluoromethylbenzoate (10.5 g) as white crystals, m.p. 58° C.

By proceeding in a similar manner the following compounds were prepared:

| (R²)ₙ | R³ | X | Position of —X—R³ | m.p./ NMR |
|---|---|---|---|---|
| 4-CF₃ | 2-Cl—C₆H₄ | S | 2 | 116° C. |
| 4-CF₃ | 3-Cl—C₆H₄ | S | 2 | 50° C. |
| 4-CF₃ | 4-Cl—C₆H₄ | S | 2 | 71° C. |
| 4-CF₃ | C₆H₅ | O | 2 | Oil (a) |

Note:
(1) ¹H NMR (CDCl₃): 3.8(3H, m); 6.9(2H, d); 7.1(2H, m); 7.3(3H, m); 7.9(1H, d).

REFERENCE EXAMPLE 5

A mixture of 2-phenylsulphenyl-4-trifluoromethylbenzonitrile (9 g), concentrated sulphuric acid (27 ml) and water was heated at reflux for 10 hours. The mixture was then cooled, poured into water and extracted with dichloromethane. The organic extract was extracted with aqueous sodium hydroxide. The resulting aqueous solution was acidified with aqueous hydrochloric acid to pH 1. The suspension was extracted with dichloromethane, dried over anhydrous sodium sulphate, filtered and after evaporation of the dichloromethane, 2-phenylsulphenyl-4-trifluoromethylbenzoic acid was obtained as a white solid (7.5 g), m.p. 161° C.

By proceeding in a similar manner the following compounds were prepared:

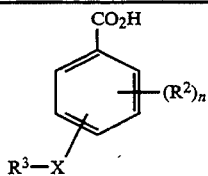

| $(R^2)_n$ | X | $R^3$ | Position of $-X-R^3$ | m.p. |
|---|---|---|---|---|
| 4-CF$_3$ | S | 2-Cl—C$_6$H$_4$ | 2 | 159° C. |
| 4-CF$_3$ | S | 3-Cl—C$_6$H$_4$ | 2 | 151° C. |
| 4-CF$_3$ | S | 4-Cl—C$_6$H$_4$ | 2 | 158° C. |
| 4-CF$_3$ | O | C$_6$H$_5$ | 2 | 131° C. |

REFERENCE EXAMPLE 6

A mixture of 2-nitro-4-trifluoromethylbenzonitrile (8.64 g), thiophenol (4.4 g) and potassium carbonate (6.9 g) in acetonitrile was heated at reflux for 4 hours. After cooling, the mixture was poured into water and extracted with dichloromethane. The organic extract was dried over anhydrous sodium sulphate, filtered and concentrated under reduced pressure. The residue was triturated with hexane to give 2-phenylsulphenyl-4-trifluoromethylbenzonitrile as a white solid (9.5 g), m.p. 51° C.

By proceeding in a similar manner the following compounds were prepared:

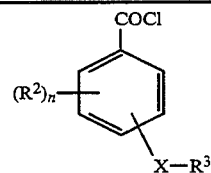

| $(R^2)_n$ | Position of $-X-R^3$ | X | $R^3$ | m.p. |
|---|---|---|---|---|
| 4-CF$_3$ | 2 | S | 2-Cl—C$_6$H$_4$ | 57° C. |
| 4-CF$_3$ | 2 | S | 3-Cl—C$_6$H$_4$ | Oil |
| 4-CF$_3$ | 2 | S | 3-Cl—C$_6$H$_4$ | 90° C. |
| 4-CF$_3$ | 2 | O | C$_6$H$_5$ | 84° C. |

REFERENCE EXAMPLE 7

A mixture of 3,4-dichloro-2-phenylsulphenylbenzoic acid (25.0 g), methanol and concentrated sulphuric acid (5 ml) was heated at reflux for 22 hours. Water was added and the mixture concentrated. The residue was taken up in ethyl acetate, washed with aqueous sodium bicarbonate, dried over anhydrous magnesium sulphate and filtered. The solvent was evaporated and the oil purified by chromatography on silica, using a mixture of cyclohexane, ether and toluene to give methyl 3,4-dichloro-2-phenylsulphenylbenzoate (13.8 g) as a clear oil, $^1$H NMR (CDCl$_3$) 3.7 (3H,s), 7.1 (5H,m), 7.4(2H, m).

REFERENCE EXAMPLE 8

A mixture of magnesium (0.80 g) and a crystal of iodine in methanol was heated at reflux for 1.5 hours. t-Butyl 3-cyclopropyl-3-oxopropanoate (5.6 g) was added and the mixture heated at reflux for a further 1 hour. The mixture was evaporated and the residue dissolved in toluene. 2-Methylsulphonyl-3-phenylsulphenylbenzoyl chloride (9.9 g) was added and the mixture stirred for 40 hours. 2N Hydrochloric acid and ethyl acetate were added and the organic phase was washed with water, dried over sodium sulphate, filtered and evaporated. The resulting solid was recrystallised from propan-2-ol giving 9.1 g of t-butyl 2-cyclopropylcarbonyl-3-(2-methylsulphonyl-3-phenylsulphenylphenyl)-3-oxopropanoate as a white powder.

By proceeding in a similar manner the following compounds were prepared:

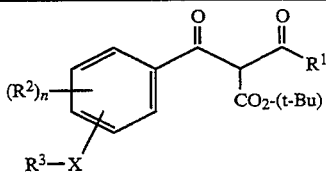

| $R^1$ | $(R^2)_n$ | X | $R^3$ | Position of $-X-R^3$ |
|---|---|---|---|---|
| Cp | 2-MeSO$_2$-4-Cl | S | C$_6$H$_5$ | 3 |
| Cp | 2-MeSO$_2$-4-Cl | O | C$_6$H$_5$ | 3 |

Benzoyl chlorides were prepared by the reaction of the corresponding benzoic acids with thionyl chloride, for example as described below.

REFERENCE EXAMPLE 9

A mixture of 2-methylsulphonyl-3-phenylsulphenylbenzoic acid and N,N-dimethylformamide (0.25 ml) in thionyl chloride was heated at reflux for 1.25 hours. The solution was evaporated to give 9.9 g of 2-methylsulphonyl-3-phenylsulphenylbenzoyl chloride as a pale yellow oil which was used directly in the next step without further purification.

By proceeding in a similar manner the following compounds were prepared:

| $(R^2)_n$ | X | $R^3$ | Position of $-X-R^3$ |
|---|---|---|---|
| 2-MeSO$_2$-4-Cl | S | C$_6$H$_5$ | 3 |
| 2-MeSO$_2$-4-Cl | O | C$_6$H$_5$ | 3 |

REFERENCE EXAMPLE 10

A mixture of methyl 2-methylsulphonyl-3-phenylsulphenylbenzoate (8.3 g), ethanol (50 ml) and 2N sodium hydroxide (25 ml) was heated at reflux for one hour and then added to water. The inorganic phase was washed with ethyl acetate, acidified with concentrated hydrochloric acid and extracted with ethyl acetate. This organic phase was dried over sodium sulphate, filtered and evaporated giving 7.9 g of 2-methylsulphonyl-3-phenylsulphenylbenzoic acid as a white solid, m.p. 185.4°–186.0° C.

REFERENCE EXAMPLE 11

A mixture of methyl 3-fluoro-2-methylsulphonylbenzoate (10.9 g), potassium carbonate (7.8 g) and thiophenol (5.4 g) in N,N-dimethylformamide was stirred at 25° C. for six hours. Water and ethyl acetate were added and the resulting solid collected by filtration and combined with the solid obtained from washing the organic phase of the flitrate with brine, drying over magnesium sulphate, filtering and evaporating. This product was recrystallised from ethyl acetate to give 7.0 g of methyl 2-methylsulphonyl-3-phenylsulphenylbenzoate as white crystals, mp 151.1° C.

REFERENCE EXAMPLE 12

A mixture of methyl 3-fluoro-2-methylsulphenylbenzoate (14.0 g) and 3-chloroperbenzoic acid (50–60%, 55.0 g) in dichloromethane was stirred at 25° C. for 1.5 hours. 1M Sodium metabisulphite was added and the organic phase washed with sodium bicarbonate and brine, dried over sodium sulphate, filtered and evaporated. The product was recrystallised from ethyl acetate to give 8.6 g of methyl 3-fluoro-2-methylsulphonylbenzoate as white crystals, m.p. 116.2° C.

REFERENCE EXAMPLE 13

Approximately 12.6 g of methanethiol was dissolved in N,N-dimethylformide. Potassium carbonate (41.5 g) and methyl 2,3-difluorobenzoate (43.1 g) were added and the mixture stirred at 25° C. for 27 hours. Saturated ammonium chloride was added and the mixture partitioned between ether and water. The organic phase was washed with water, dried over magnesium sulphate, filtered and evaporated. The product was obtained by distillation to give 35.5 g of methyl 3-fluoro-2-methylsulphenylbenzoate, b.p. 140° C. (9mm Hg) as a clear oil. NMR (CDCl$_3$) 2.5(3H, d), 3.9(3H,s), 7.2(1H,m), 7.3(1H,m), 7.5(1H, m).

REFERENCE EXAMPLE 14

A mixture of methyl 4-chloro-2-nitrobenzoate (17 g), thiophenol (10.4 g) and potassium carbonate (13.1 g) in acetone was heated at reflux for eight hours. Water was added and the mixture extracted with ethyl acetate. The organic phase was washed with brine, dried over magnesium sulphate, filtered and evaporated. The product was purified by chromatography on silica using a mixture of ether and hexane to give, after evaporation of the solvent, 13.6 g of methyl 4-chloro-2-phenylsulphenylbenzoate as a white solid, m.p.58.7° C.

By proceeding in a similar manner the following compounds were prepared:
methyl 3-chloro-2-(3-chlorophenylsulphenyl)benzoate, m.p. 58.4° C;
methyl 3-chloro-2-(3-methoxyphenylsulphenyl)benzoate, m.p. 72.8° C.

REFERENCE EXAMPLE 15

A mixture of methyl 4-chloro-2-nitrobenzoate (25 g), thiophenol (20.4 g) and potassium carbonate (17.6 g) in N,N-dimethylformamide was stirred at 120° C. for five hours. Water was added and the mixture extracted with ethyl acetate. The organic phase was washed with water, dried over magnesium sulphate, filtered and evaporated. The product was recrystallised from cyclohexane to give 3.0 g of methyl 2,4-bis(phenylsulphenyl)benzoate as a beige solid, m.p. 123.9° C.

REFERENCE EXAMPLE 16 n-Butyllithium (2.5M in hexane, 120 ml) was added over 2 hours to a stirred solution of 3,4-dichlorobenzoic add (2:5 g) in tetrahydrofuran at −70° C. The mixture was stirred for 24 hours at −70° C. and then diphenyldisulphide (38 g) was added in tetrahydrofuran over 45 mins. The mixture was stirred for 16 hours at −70° C. and then at room temperature for 24 hours. The beige suspension was poured into water and the resulting solution was washed with cyclohexane and then ether. The organic layers were combined, washed with brine, dried over magnesium sulphate, filtered and evaporated to give 32.7 g of 3,4-dichloro-2-phenylsulphenylbenzoic acid as a white solid.

REFERENCE EXAMPLE 17

Phenol (2.26 g) was added to a mixture of 4-chloro-3-fluoro-2-methylsulphonylbenzoic acid (4.46 g) and lithium hydroxide monohydrate (1.65 g) in N,N-dimethylformamide and the mixture was stirred and heated at 100° C. overnight. It was cooled, poured into water and acidified to pH 1, extracted with ethyl acetate and the organic phase extracted into aqueous sodium bicarbonate solution. The aqueous layer was acidified to pH 1 and extracted with ethyl acetate, washed with water, dried (magnesium sulphate) and filtered. The filtrate was evaporated to dryness to give 4-chloro-2-methylsulphonyl-3-phenoxybenzoic acid (4.06 g) as an off-white solid m.p. 231°–235° C.

REFERENCE EXAMPLE 18

Thiophenol (2.64 g) was added to a mixture of 4-chloro-3-fluoro-2-methylsulphonylbenzoic acid (4.0 g) and lithium hydroxide monohydrate (1.65 g) in N,N-dimethylformamide. The mixture was stirred at room temperature overnight. It was diluted with water and acidified to pH 1. The resultant solid was filtered off and washed with water. It was triturated with n-hexane and filtered then with dichloromethane and filtered to give 4-chloro-2-methylsulphonyl-3-(phenylsulphenyl)-benzoic add (4.77 g) as a white solid, m.p. 210°–213° C.

REFERENCE EXAMPLE 19

Hydrogen peroxide (30%; 66 ml) was added to a suspension of 4-chloro-3-fluoro-2-(methylsulphenyl)-benzoic acid (2.5 g) and concentrated sulphuric acid (1.5 ml) in acetic acid. The mixture was heated slowly to 80° C. and stirred and heated at that temperature overnight. It was cooled to room temperature and treated with sodium metabisulphite (45 g). It was evaporated and the residue was treated with water and acidified to pH 1. It was extracted with ethyl acetate, washed with water, dried (MgSO$_4$) and filtered. The filtrate was evaporated to dryness to give 4-chloro-3-fluoro-2-methylsulphonylbenzoic acid (24 g) as an off white solid m.p. 196°–200° C.

REFERENCE EXAMPLE 20

Butyllithium (2.5M in hexane; 180 ml) was added dropwise with stirring to a cooled solution of 4-chloro-3-fluorobenzoic acid (37.5 g) in tetrahydrofuran at −40° C. for 3 hours. A solution of dimethyldisulphide (60.5 g) in tetrahydrofuran was added and the mixture was stirred at room temperature overnight. Hydrochloric acid (2M) was added and the layers were separated. The aqueous layer was extracted with ether and the combined organic layers were extracted with aqueous sodium hydroxide solution (2M). The aqueous layer was acidified to pill and extracted with ether, washed with water, dried (sodium sulphate) and filtered. The flitrate was evaporated to dryness and the residue was triturated with n-hexane and filtered to give 4-chloro-3- fluoro-2-(methylsulphenyl)benzoic acid (32.84 8) as a yellow solid m.p. 149.5°-150.5° C.

According to a feature of the present invention, there is provided a method for controlling the growth of weeds (i.e. undesired vegetation) at a locus which comprises applying to the locus a herbicidally effective amount of at least one isoxazole derivative of formula (I). For this purpose, the isoxazole derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranathus retroflexus, Bidens pilosa, Chenopodium album, Galium aparine, Ipomoea spp.* e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crus-galli, Sorghum bicolor, Eleusine indica* and *Setaria spp,* e.g. *Setaria faberii* or *Setaria viridis,* and sedges, for example, *Cyperus esculentus.*

The amounts of compounds of formula (I) applied vary with the nature of the weeds, the compositions used, the time of application, the climatic and edaphic conditions and (when used to control the growth of weeds in crop-growing areas) the nature of the crops. Where applied to a crop-growing area, the rate of application should be sufficient to control the growth of weeds without causing substantial permanent damage to the crop. In general, taking these factors into account, application rates between 0.01 kg and 5 kg of active material per hectare .give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion., e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non- directional fashion (e.g. by directional or non-directional spraying) to the weeds or to the soil in which they are expected to appear, before or after planting of :he trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes/.n which a total herbicidal effect is frequently desired, the active compounds are normally applied at dosage rates higher than those used [n crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the isoxazole derivatives of formula (I), in association with, and preferably homogeneously dispersed in, one or more compatible agriculturally-acceptable diluents or carriers and/or surface active agents [i.e. diluents or carriers and/or surface active agents of the .type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or nonionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and diocryl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminum silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and fight aromatic and naphthenic fractions of petroleum (and mixtures of these diluents). Surface-active agents, which may be present in the liquid compositions, may be ionic or nonionic (for example of the types described above) and may, when liquid, a/so serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise Specified, the following percentages are by weight. Preferred herbicidal compositions according to the present invention are:

aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 4.0% of sodium carbonate and from 0 to 88% of solid diluent;

liquid water soluble concentrates which comprise from 5 to 50%, e.g. 10 to 30%, of one or more compounds of formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%. e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil[3,5-dibromo-4-hydroxybenzonitrile], chlortoluron [N'-(3-chloro-4-methylphenyl)-N,N-dimethylurea], cyanazine [2-chloro4-( 1-cyano-1- methylethylamino)-6-ethylamino-1,3,5-triazine], 2,4-D [2,4-dichlorophenoxy-acetic acid], dicamba [3,6-dichloro-2-methoxybenzoic acid], difenzoquat [1,2- dimethyl-3,5-diphenylpyraazolium salts], flampropmethyl [methyl N-2-(N-benzoyl-3-chloro-4-fluoroanilino)-propionate], fluometuron [N'-(3-trifluoromethylphenyl)-N,N-dimethylurea], isoproturon[N'-(4-isopropylphenyl)-N,N-dimethylurea], insecticides, e.g. synthetic pyrethroids, e.g. permethrin and cypermethrin and fungicides, e.g. carbamates, e.g. methyl N-(1-butyl-carbamoyl-benzimidazol-2-yl)carbamate, and triazoles e.g. 1-(4-chloro-phenoxy)-3,3- dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the isoxazole derivatives of formula (I) or, as is preferred, a herbicidal composition as hereinbefore described, and preferably a herbicidal concentrate which must be diluted before use, comprising at least one of the isoxazole derivatives of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain mounts of the isoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal application according to the following procedures.

METHOD OF USE OF HERBICIDAL COMPOUNDS a) General

Appropriate quantities of the compounds used to treat the p/ants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b)Weed control: Pre-emergence

The seeds were sown in 70 mm square, 75 mm deep plastic pots in non-sterile soil. The quantities of seed per pot were as follows:

|  | Approx number of seeds/pot |
|---|---|
| Weed species | |
| 1) Broad-leafed weeds | |
| *Abutilon theophrasti* | 10 |
| *Amaranthus retroflexus* | 20 |
| *Galium aparine* | 10 |
| *Ipomoea purpurea* | 10 |
| *Sinapis arvensis* | 15 |
| *Xanthium strumarium* | 2. |
| 2) Grass weeds | |
| *Alopecurus myosuroides* | 15 |
| *Avena fatua* | 10 |
| *Echinochloa crus-galli* | 15 |
| *Setaria viridis* | 20. |
| 3) Sedges | |
| *Cyperus esculentus* | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

|  | Number of plants per pot | Growth stage |
|---|---|---|
| Weed species | | |
| 1) Broad leafed weeds | | |
| *Abutilon theophrasti* | 3 | 1–2 leaves |
| *Amaranthus retroflexus* | 4 | 1–2 leaves |
| *Galium aparine* | 3 | 1st whorl |
| *Ipomoea purpurea* | 3 | 1–2 leaves |
| *Sinapis arvensis* | 4 | 2 leaves |
| *Xanthium strumarium* | 1 | 2–3 leaves. |
| 2) Grass weeds | | |
| *Alopecurus myosuroides* | 8–12 | 1–2 leaves |
| *Avena fatua* | 12–18 | 1–2 leaves |
| *Echinochloa crus-galli* | 4 | 2–3 leaves |
| *Setaria viridis* | 15–25 | 1–2 leaves. |
| 3) Sedges | | |
| *Cyperus esculentus* | 3 | 3 leaves. |
| Crops | | |
| 1) Broad leafed | | |
| Cotton | 2 | 1 leaf |
| Soya | 2 | 2 leaves. |
| Grass | | |

-continued

|  | Number of plants per pot | Growth stage |
|---|---|---|
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone a/one.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention, used at 4 kg/ha or less, have shown an excellent level of herbicidal activity together with crop tolerance on the weeds used in the foregoing experiments.

When applied pre- or post-emergence at 1000 g/ha compounds 1 to 23 gave at least 90% reduction in growth of one or more of the weed species.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound of the formula:

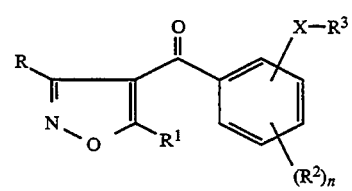

wherein
R is hydrogen or $-CO_2R^4$;
$R^1$ is:
    straight- or branched-chain alkyl having up to 6 carbon atoms, optionally substituted by one or more halogen; or
    cycloalkyl having from 3 to 6 carbon atoms, optionally substituted by one or more $R^5$ or one or more halogen;
$R^2$ is:
    halogen;
    straight- or branched-chain alkyl having up to 6 carbon atoms, optionally substituted by one or more halogen;
    straight- or branched-chain alkyl having up to 6 carbon atoms substituted by one or more $-OR^5$; or
    a member selected from the group consisting of nitro, cyano, $-CO_2R^4$, $-S(O)_pR^6$, $-O(CH_2)_rOR^5$ and $-OR^5$;
$R^3$ is phenyl optionally substituted by from one to five $R^7$ which can be the same or different;

X is oxygen or —S(O)$_q$—;

n is zero or an integer from one to four, provided that when n is greater than one, the R$^2$ groups can be the same or different;

each of R$^4$ and R$^5$, which can be the same or different, is straight- or branched-chain alkyl having up to 6 carbon atoms, optionally substituted by one or more halogen;

R$^6$ is:

straight- or branched-chain alkyl having up to 6 carbon atoms, optionally substituted by one or more halogen; or phenyl optionally substituted by one or more R$^7$ which can be the same or different;

R$^7$ is:

halogen;

straight- or branched-chain alkyl group having up to three carbon atoms, optionally substituted by one or more halogen; or a member selected from the group consisting of nitro, cyano, —OR$^5$ and —S(O)$_p$R$^6$;

p is zero, one or two;

q is zero, one or two; and r is one, two or three.

2. A compound according to claim 1, wherein R$^6$ is straight- or branched-chain alkyl having up to 6 carbon atoms, optionally substituted by one or more halogen.

3. A compound according to claim 1, wherein —XR$^3$ or an R$^2$ substituent is located in the 2-position of the benzoyl ring.

4. A compound according to claim 2, wherein —XR$^3$ or an R$^2$ substituent is located in the 2-position of the benzoyl ring.

5. A compound according to claim 1, wherein: R$^1$ is straight- or branched-chain alkyl having up to three carbon atoms; or cyclopropyl optionally substituted by one R$^5$;

R$^2$ is:

halogen;

straight- or branched-chain alkyl having up to 6 carbon atoms, optionally substituted by one or more halogen;

straight- or branched-chain alkyl having up to 6 carbon atoms substituted by one or more —OR$^5$; or a member selected from the group consisting of cyano, —CO$_2$R$^4$, —S(O)$_p$R$^6$, —O(CH$_2$)$_r$OR$^5$ and —OR$^5$;

n is zero, one or two;

R$^4$ is straight- or branched-chain alkyl having up to six carbon atoms;

R$^5$ is straight- or branched-chain alkyl having up to three carbon atoms, optionally substituted by one or more halogen; and R$^6$ is straight- or branched-chain alkyl having up to three carbon atoms.

6. A compound according to claim 5, wherein —XR$^3$ or an R$^2$ substituent is located in the 2-position of the benzoyl ring.

7. A compound according to claim 1, wherein R$^2$ is —S(O)$_p$R$^6$ and one of p and q is zero.

8. A compound according to claim 3, wherein R$^2$ is —S(O)$_p$R$^6$ and one of p and q is zero.

9. A compound according to claim 5, wherein R$^2$ is —S(O)$_p$R$^6$ and one of p and q is zero.

10. A compound according to claim 1, wherein:

R$^1$ is methyl, isopropyl, 1-methylcyclopropyl or cyclopropyl;

R$^2$ is:

halogen;

straight- or branched-chain alkyl having up to three carbon atoms, optionally substituted by one or more halogen;

straight- or branched-chain alkyl having up to three carbon atoms substituted by one or more —OR$^5$;

—OR$^5$; or

—S(O)$_p$R$^6$;

X is —S(O)$_q$—;

n is one or two;

R$^5$ is methyl or ethyl, optionally substituted by one or more halogen; and

R$^6$ is methyl or ethyl.

11. A compound according to claim 10, wherein —XR$^3$ or an R$^2$ substituent is located in the 2-position of the benzoyl ring.

12. A compound according to claim 10, wherein R$^4$ is straight- or branched-chain alkyl having up to six carbon atoms.

13. A compound according to claim 12, wherein —XR$^3$ or an R$^2$ substituent is located in the 2-position of the benzoyl ring.

14. A compound according to claim 10, wherein R$^2$ is —S(O)$_p$R$^6$ and one of p and q is zero.

15. A compound according to claim 1, wherein at least one of the 5- and 6-positions of the benzoyl ring is unsubstituted.

16. A compound according to claim 3, wherein at least one of the 5- and 6-positions of the benzoyl ring is unsubstituted.

17. A compound according to claim 5, wherein at least one of the 5- and 6-positions of the benzoyl ring is unsubstituted.

18. A compound according to claim 7, wherein at least one of the 5- and 6-positions of the benzoyl ring is unsubstituted.

19. A compound according to claim 10, wherein at least one of the 5- and 6-positions of the benzoyl ring is unsubstituted.

20. A compound according to claim 10, wherein:

R$^1$ is cyclopropyl;

R$^2$ is halogen, methyl, trifluoromethyl, methoxy or —S(O)$_p$R$^6$;

n is one or two;

X is —S(O)$_q$—;

R$^4$ is straight- or branched-chain alkyl having up to three carbon atoms;

R$^7$ is halogen, methyl, trifluoromethyl, nitro or —OR$^5$;

R$^5$ is methyl or ethyl; and

R$^6$ is methyl.

21. A compound according to claim 20, wherein —XR$^3$ or an R$^2$ substituent is located in the 2-position of the benzoyl ring.

22. A compound according to claim 20, wherein R$^2$ is —S(O)$_p$R$^6$ and one of p and q is zero.

23. A compound according to claim 21, wherein R$^2$ is —S(O)$_p$R$^6$ and one of p and q is zero.

24. A compound according to claim 20, wherein at least one of the 5- and 6-positions of the benzoyl ring is unsubstituted.

25. A compound according to claim 21, wherein at least one of the 5- and 6-positions of the benzoyl ring is unsubstituted.

26. A compound according to claim 22, wherein at least one of the 5- and 6-positions of the benzoyl ring is unsubstituted.

27. A compound according to claim 23, wherein at least one of the 5- and 6-positions of the benzoyl ring is unsubstituted.

28. The compound according to claim 1, which is:
5-cyclopropyl-4-(2-phenylsulphenyl-4-trifluoromethylbenzoyl)isoxazole;
5-cyclopropyl-4-(2-phenylsulphonyl-4-trifluoromethylbenzoyl)isoxazole;
5-cyclopropyl-4-(2-phenoxy-4-trifluoromethylbenzoyl)isoxazole;
5-cyclopropyl-4-[2-(3-chlorophenylsulphenyl)-4-trifluoromethylbenzoyl]isoxazole;
5-cyclopropyl-4-[2-(2-chlorophenylsulphenyl)-4-trifluoromethylbenzoyl]isoxazole;
5-cyclopropyl-4-[2-(4-chlorophenylsulphenyl)-4-trifluoromethylbenzoyl]isoxazole;
5-cyclopropyl-4-[2-(3-chlorophenylsulphonyl)-4-trifluoromethylbenzoyl]isoxazole;
5-cyclopropyl-4-[2-(4-chlorophenylsulphonyl)-4-trifluoromethylbenzoyl]isoxazole;
5-cyclopropyl-4-[2-(4-chlorophenylsulphinyl)-4-trifluoromethylbenzoyl]isoxazole;
5-cyclopropyl-4-(4-chloro-2-phenylsulphenylbenzoyl)isoxazole;
5-cyclopropyl-4-(4-chloro-2-phenylsulphonylbenzoyl)isoxazole;
5-cyclopropyl-4-[4-chloro-2-(3-chlorophenylsulphenyl)benzoyl]isoxazole;
5-cyclopropyl-4-[4-chloro-2-(3-chlorophenylsulphinyl)benzoyl]isoxazole;
5-cyclopropyl-4-[4-chloro-2-(3-chlorophenylsulphonyl)benzoyl]isoxazole;
5-cyclopropyl-4-[4-chloro-2-(3-methoxyphenylsulphenyl)benzoyl]isoxazole;
5-cyclopropyl-4-[4-chloro-2-(3-methoxyphenylsulphinyl)benzoyl]isoxazole;
5-cyclopropyl-4-[4-chloro-2-(3-methoxyphenylsulphonyl)benzoyl]isoxazole;
5-cyclopropyl-4-[2,4-bis(phenylsulphenyl)benzoyl]isoxazole;
5-cyclopropyl-4-(3,4-dichloro-2-phenylsulphenylbenzoyl)isoxazole;
5-cyclopropyl-4-(3,4-dichloro-2-phenylsulphonylbenzoyl)isoxazole;
5-cyclopropyl-4-(4-chloro-2-methylsulphonyl-3-phenoxybenzoyl)isoxazole; or
5-cyclopropyl-4-(4-chloro-2-methylsulphonyl-3-phenylsulphenylbenzoyl)isoxazole; or
5-cyclopropyl-4-(2-methylsulphonyl-3-phenylsulphenylbenzoyl)isoxazole.

29. A herbicidal composition comprising:
(a) a herbicidally effective amount of a compound of the formula wherein:
R is hydrogen or —CO$_2$R$^4$;
R$^1$ is:
straight- or branched-chain alkyl having up to 6 carbon atoms, optionally substituted by one or more halogen; or
cycloalkyl having from 3 to 6 carbon atoms, optionally substituted by one or more R$^5$ or one or more halogen;
R$^2$ is:
halogen;
straight- or branched-chain alkyl having up to 6 carbon atoms, optionally substituted by one or more halogen;
straight- or branched-chain alkyl having up to 6 carbon atoms substituted by one or more —OR$^5$; or
a member selected from the group consisting of nitro, cyano, —CO$_2$R$^4$, —S(O)$_p$R$^6$, —O(CH$_2$)$_r$OR$^5$ and —OR$^5$;
R$^3$ is phenyl optionally substituted by from one to five R$^7$ which can be the same or different;
X is oxygen or —S(O)$_q$—;
n is zero or an integer from one to four, provided that when n is greater than one, the R$^2$ groups can be the same or different;
each of R$^4$ and R$^5$, which can be the same or different, is straight- or branched-chain alkyl having up to 6 carbon atoms, optionally substituted by one or more halogen;
R$^6$ is:
straight- or branched-chain alkyl having up to 6 carbon atoms, optionally substituted by one or more halogen; or
phenyl optionally substituted by one or more R$^7$ which can be the same or different;
R$^7$ is:
halogen;
straight- or branched-chain alkyl having up to three carbon atoms, optionally substituted by one or more halogen; or
a member selected from the group consisting of nitro, cyano, —OR$^5$ and —S(O)$_p$R$^6$;
p is zero, one or two;
q is zero, one or two; and
r is one, two or three; and
(b) at least one member of the group consisting of an agriculturally acceptable inert carrier and an agriculturally acceptable surface active agent.

30. A method for controlling the growth of weeds at a locus comprising applying to said locus a herbicidally effective amount of a compound of the formula wherein:
R is hydrogen or —CO$_2$R$^4$;
R$^1$ is:
straight- or branched-chain alkyl having up to 6 carbon atoms, optionally substituted by one or more halogen; or
cycloalkyl having from 3 to 6 carbon atoms, optionally substituted by one or more R$^5$ or one or more halogen;
R$^2$ is:

halogen;

straight- or branched-chain alkyl having up to 6 carbon atoms, optionally substituted by one or more halogen;

straight- or branched-chain alkyl having up to 6 carbon atoms substituted by one or more —$OR^5$; or a member selected from the group consisting of nitro, cyano, —$CO_2R^4$, —$S(O)_pR^6$, —$O(CH_2)_rOR^5$ and —$OR^5$;

$R^3$ is phenyl optionally substituted by from one to five $R^7$ which can be the same or different;

X is oxygen or —$S(O)_q$—;

n is zero or an integer from one to four, provided that when n is greater than one, the $R^2$ groups can Be the same or different;

each of $R^4$ and $R^5$, which can Be the same or different, is straight- or branched-chain alkyl having up to 6 carbon atoms, optionally substituted By one or more halogen;

$R^6$ is:

straight- or branched-chain alkyl having up to 6 carbon atoms, optionally substituted by one or more halogen; or phenyl optionally substituted by one or more $R^7$ which can be the same or different;

$R^7$ is:

halogen;

straight- or branched-chain alkyl having up to three carbon atoms, optionally substituted by one or more halogen; or a member selected from the group consisting of nitro, cyano, —$OR^5$ and —$S(O)_pR^6$;

p is zero, one or two;

q is zero, one or two; and r is one, two or three.

31. A method according to claim 30, wherein the locus is an area used, or to be used, for the growing of crops and the compound of formula (I) is applied at an application rate of from about 0.01 kg to about 4.0 kg per hectare.

32. A method for controlling the growth of weeds at a locus comprising applying to said locus a herbicidally effective mount of a composition as claimed in claim 29.

33. A method according to claim 32, wherein the locus is an area used, or to be used, for the growing of crops and the composition is applied at an application rate of from about 0.01 kg to about 4.0 kg of compound of formula (I) per hectare.

* * * * *